United States Patent
McPherson et al.

(10) Patent No.: US 7,087,034 B2
(45) Date of Patent: Aug. 8, 2006

(54) VASCULAR SHUNT WITH AUDIO FLOW INDICATION

(76) Inventors: William E. McPherson, 14605 Anchoret Rd., Tampa, FL (US) 33624; Walter Smithwick, 3500 Timuquana Rd., Jacksonville, FL (US) 32210

( * ) Notice: Subject to any disclaimer, the term of this patent is extended or adjusted under 35 U.S.C. 154(b) by 435 days.

(21) Appl. No.: 10/247,601

(22) Filed: Sep. 19, 2002

(65) Prior Publication Data
US 2004/0059278 A1   Mar. 25, 2004

(51) Int. Cl.
*A61M 5/00* (2006.01)
*A61B 5/02* (2006.01)
*A61F 2/06* (2006.01)

(52) U.S. Cl. .................. 604/8; 604/96.01; 600/504; 623/1.31

(58) Field of Classification Search ........ 210/645–646, 210/739, 745, 746, 97; 604/4.01, 6.1, 6.16, 604/101.05, 96.01, 101.01, 101.03, 264, 604/66, 26–28, 509, 7–10, 118; 623/1.12, 623/1.25, 1.3, 1.31; 73/861.18; 600/485, 600/486, 500, 504, 301, 381
See application file for complete search history.

(56) References Cited

U.S. PATENT DOCUMENTS

| | | | |
|---|---|---|---|
| 3,516,408 A * | 6/1970 | Montanti ........................ 604/8 |
| 3,958,458 A * | 5/1976 | Foreman et al. ......... 73/861.18 |
| 3,991,767 A * | 11/1976 | Miller et al. .................... 604/8 |
| 4,230,119 A * | 10/1980 | Blum .......................... 606/194 |
| 4,312,238 A | 1/1982 | Rey |
| 4,566,462 A | 1/1986 | Janssen |
| 4,709,690 A | 12/1987 | Haber |
| 4,712,551 A | 12/1987 | Rayhanabad |
| 4,731,055 A * | 3/1988 | Melinyshyn et al. .. 604/100.02 |
| 4,986,276 A | 1/1991 | Wright |
| 5,259,386 A | 11/1993 | Sharkawy |
| 5,320,105 A | 6/1994 | Bonnefous et al. |
| 5,363,852 A * | 11/1994 | Sharkawy ................... 600/461 |
| 5,562,098 A | 10/1996 | Lerner |
| 5,957,866 A | 9/1999 | Shapiro et al. |
| 5,967,989 A | 10/1999 | Cimochowski et al. |
| 6,086,557 A * | 7/2000 | Morejohn et al. ....... 604/96.01 |
| 6,127,410 A | 10/2000 | Duhaylongsod |
| 6,153,109 A | 11/2000 | Krivitski |
| 6,398,764 B1 * | 6/2002 | Finch et al. ................. 604/284 |

OTHER PUBLICATIONS

Online Product brochure for HT331 Neurosurgery Flow-QC Meter, by Transonic Systems Inc. Rev. Feb. 9, 1999.
Product brochure for vascular products entitled *A proven concept in Vascular Surgery*, by Ideas for Medicine Inc. date unknown.
Ian L. Gordon, MD, PhD., et al., "Intraoperative Measurement of Javid Shunt Flow With Transit-time Ultrasound", Annals of Vascular Surgery vol. 8, No. 6, 1994, pp. 571-577.

* cited by examiner

*Primary Examiner*—Patricia Bianco
*Assistant Examiner*—Leslie Deak
(74) *Attorney, Agent, or Firm*—Tarolli, Sundheim, Covell & Tummino LLP

(57) ABSTRACT

A vascular shunt apparatus (10) includes a tubular member having first and second end portions (16, 20) and an aperture extending through the first and second end portions (16, 20). A transducer (64) can be associated with the tubular member to provide a signal in response to the flow of fluid through the tubular member. One or both of the end portions (16, 20) also can be adapted to form respective sealing connections with different parts of a patient's vascular system.

20 Claims, 3 Drawing Sheets

VASCULAR SHUNT WITH AUDIO FLOW INDICATION

TECHNICAL FIELD

The present invention relates generally to a vascular shunt for use in surgical procedures. The present invention also relates generally to an apparatus for audibly monitoring fluid flow in a vascular shunt.

BACKGROUND OF THE INVENTION

Vascular shunts have been utilized in surgical procedures for by-passing a section of a blood vessel. Such vascular shunts channel blood flow from the heart into a tubular passageway past a section of a blood vessel upon which surgery is to be performed. The blood is reintroduced into the same or a different blood vessel at a downstream location, thereby by-passing a portion of the blood vessel to enable that portion to be surgically repaired.

Also, in typical blood flow measuring devices, flow data measurements are obtained as operational intelligence tools. Many costly, delicate, and complex methods exist for scientific or medical investigation of steady and unsteady blood flow during a surgical procedure. However many conventional devices are expensive, complex, or otherwise are not wholly satisfactory.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

An example embodiment of the vascular shunt of the present invention includes a tubular member having first and second end portions spaced apart by an intermediate portion. The end portions are adapted to provide generally sealing connections with different parts of a patient's vascular system. A transducer, such as a piezo-electric element, can be operatively associated with the tubular member to provide an electrical signal indicative of blood flowing through the shunt. For example, the transducer is sensitive to pressure variations caused by flow of blood through the shunt. The electrical signal can, in turn, be amplified and supplied to an audio speaker to provide an audible indication of whether blood is flowing normally through the shunt. For example, if the shunt were to clog (in whole or in part) so as to effect a substantial change in the flow of blood through the shunt, the surgeon could discern this from the audible indication.

In a particular example of the shunt, one of its end portions (e.g., the second end portion) has an enlarged cross-sectional area or bulge, such as spaced from the opening thereof. The enlarged cross-sectional area helps form a sealing connection with an interior portion of a blood vessel when inserted therein. According to another aspect, the opening at the second end portion can be axially tapered (or chamfered) at an angle to facilitate insertion of the second end portion into the blood vessel.

According to another aspect of the present invention, the outlet portion can also have an opening located between the enlarged cross-sectional area and a distal end of the second end portion. The opening mitigates occlusion of the blood vessel relative to the second opening.

BRIEF DESCRIPTION OF THE DRAWINGS

The foregoing and other features of the present invention will become apparent to one skilled in the art to which the present invention relates upon consideration of the following description of the invention with reference to the accompanying drawings.

FIG. 4 is a schematic detail of part of the apparatus of FIG. 1.

DETAILED DESCRIPTION

Figure 1:
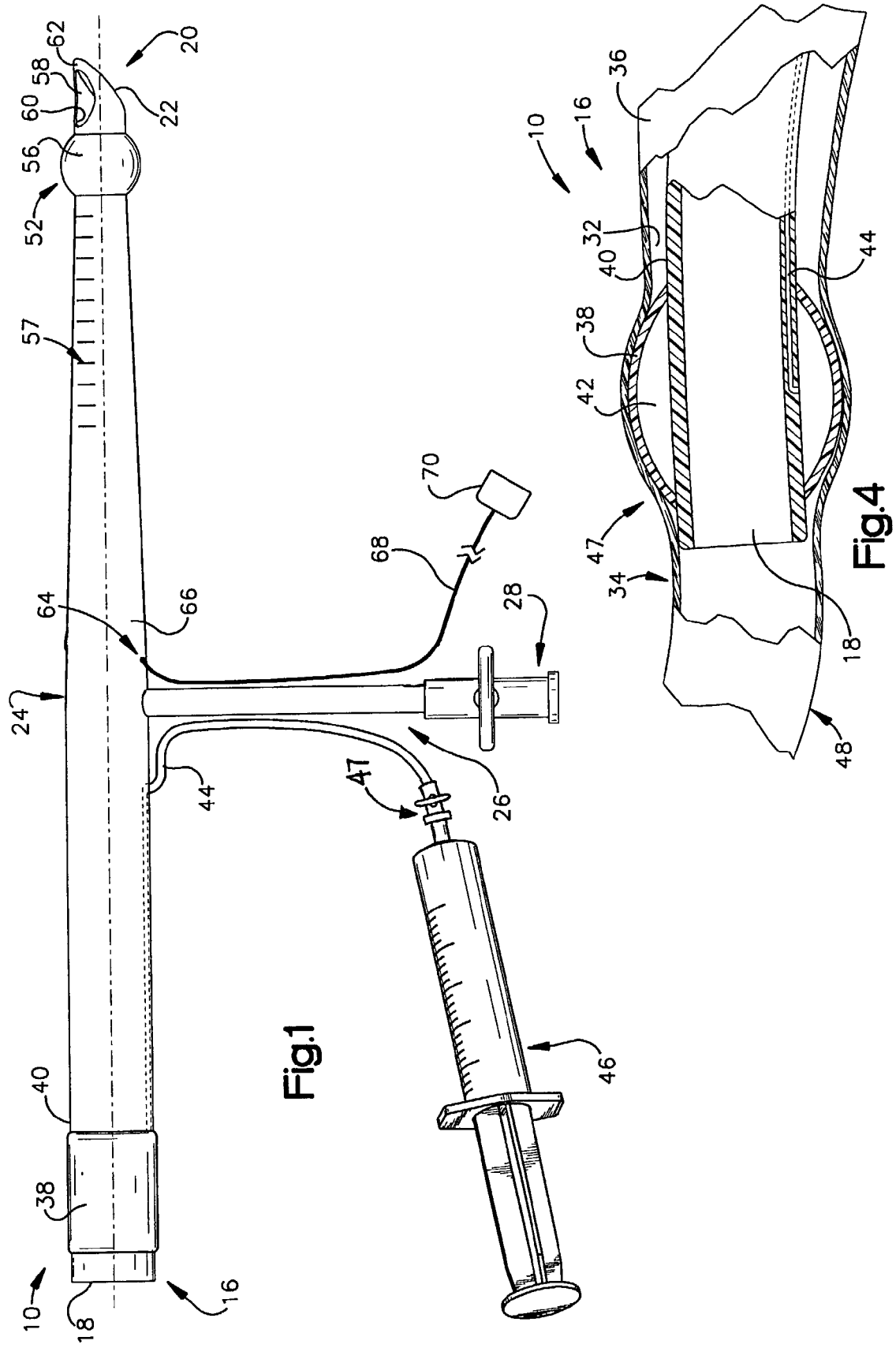
FIG. 1 is a schematic view of an apparatus in accordance with the present invention.

The present invention relates generally to a vascular shunt 10 for diverting blood flow during certain surgical bypass procedures. For example, the shunt 10 can be utilized to divert carotid blood flow during surgery, such as to remove plaque build-up on the internal wall of the carotid artery. A transducer is operatively associated with the shunt 10 to detect the status of blood flow through the shunt. The transducer provides an electrical signal that can be converted into audio to provide a tangible indication of whether or not fluid (e.g., blood) is flowing through the shunt. By using a single transducer to detect flow of blood, the cost of the overall system and associated electronics can be substantially reduced relative to conventional systems.

The vascular shunt 10 includes a generally cylindrical, flexible tube. For an example of a carotid shunt, the tube is typically about 12" in length; although it can be provided in other lengths greater than or less than 12". The vascular shunt 10 has a first end (or inlet) portion 16 with an inlet opening 18, a second end (or outlet) portion 20 with an outlet opening 22, and an intermediate portion 24 fluidly interconnecting the inlet portion and the outlet portion.

The diameter of the shunt at the inlet portion 16 can have an outer diameter that is greater than the diameter at the outlet portion 20, such that the cross-sectional diameter of the shunt tapers from the inlet to the outlet. By way of particular example, the inlet portion 16 can have an inner diameter of about 0.14" and an outer diameter of about 0.24", for example. The vascular shunt 10 can taper to an inner diameter of about 0.070" and an outer diameter of about 0.110" at the outlet portion 20. It is to be understood that other relative dimensions of the tubular member between the inlet and outlet portions can be utilized depending, for example, on the size of the patient and where the shunt to utilized in the patient.

The opening 22 at the second end portion 20 further can be tapered to facilitate its insertion into a blood vessel. For example, a distal end of the end portion 20 can have an angled end surface angled axially relative to the tubular member. The tapered end can be formed as part of the shunt (e.g., during a dipping process or an injection molding process) or the distal end can be cut at an appropriate angle, such as less that or equal to about 60° (e.g., about 45°), relative to its longitudinal axis to define the tapered opening 22. The tapered opening 22 thus defines a generally elliptical outlet at the angled end surface of the shunt 10, which outlet is larger than a cross-section of the tube near the second end portion 20. The tapered opening 22 facilitates insertion of the end portion 20 into the blood vessel, such as shown in FIGS. 2 and 3.

The vascular shunt 10 further includes a tubular branch portion 26 extending from the intermediate portion 24 and terminating with a manually operable valve 28, such as a one-way stopcock. For example, the stopcock can be used to bleed air out of the vascular shunt 10 when positioning the vascular shunt at the surgical site.

Figure 2:
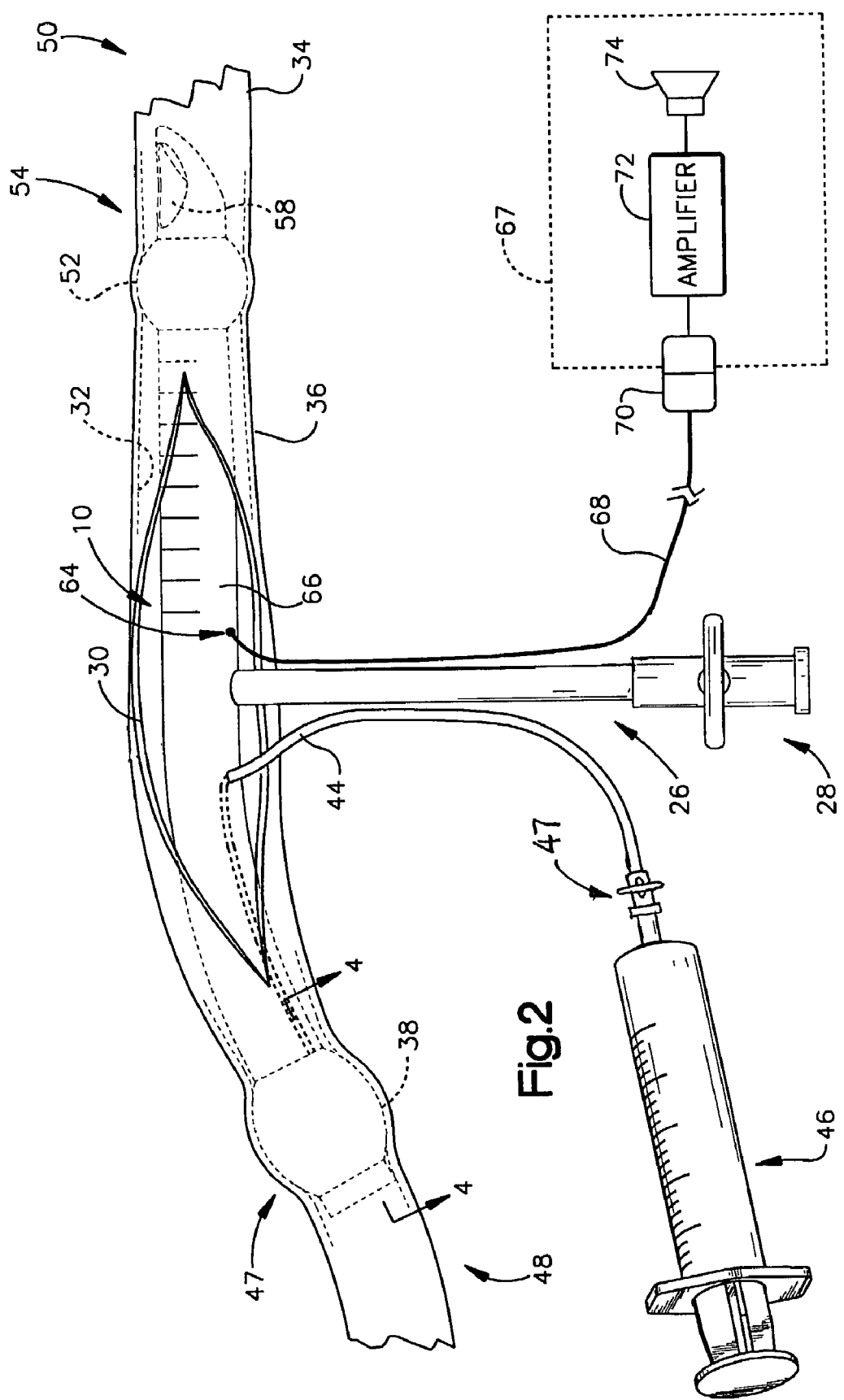
FIG. 2 is a schematic view of the apparatus of FIG. 1 in position at a surgical site.
Figure 3:
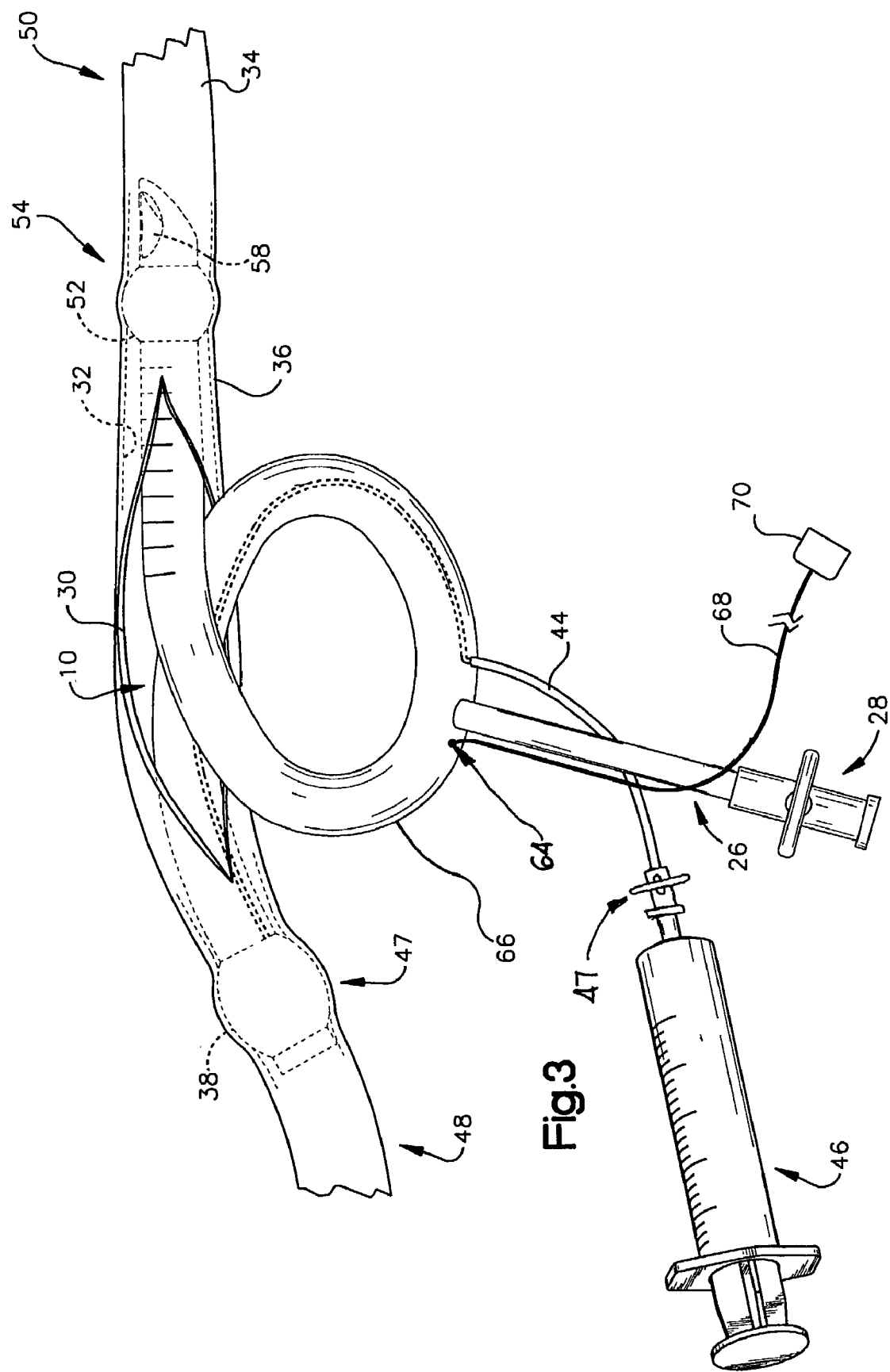
FIG. 3 is a schematic view of the apparatus of FIG. 1 in a different position at a surgical site.

With reference to FIGS. 2 and 3, the inlet portion 18 is adapted for insertion into an incision 30 surgically formed in the wall 32 of a blood vessel 34, such as at a location upstream relative to a portion 36 of the blood vessel to be operated upon. The incision 30 is one continuous cut exposing the surgical site and the points of insertion of the inlet portion 16 and the outlet portion 20 of the vascular shunt 10.

As viewed in FIG. 4, the inlet portion 16 includes an inflatable collar 38, such as a balloon, disposed about the tubular shunt near the inlet opening 18 of the inlet portion. For example, the collar 38 substantially circumscribes a length of the shunt at a location spaced from the inlet opening 18 and is sealed to an outer wall 40 of the inlet portion by a suitable means, such as an adhesive.

The collar 38 defines an annular, inflatable chamber 42 (FIG. 4) that encircles at least a substantial part of the inlet portion 16. A flexible tube 44 is in fluid communication with the collar 38 and defines a path of flow into and out of the chamber 42. The flexible tube 44 is used for inflating and deflating the collar 38 connected thereto. As depicted in FIGS. 1, 2 and 3, a lumen can extend longitudinally through a portion of the shunt 10, such as between the inner and outer sidewalls thereof. The lumen provides a substantially non-obstructive passage, such as to permit the tube 44 to connect with the inflatable collar 38 located adjacent the inlet portion 16. Another portion of the tube 44 extends away from the intermediate portion 24 external to the vascular shunt 10, such as at a location adjacent branch portion 26 for facilitating access to the tube during the surgical procedure. A syringe 46 can be connected to the flexible tube 44 via a stopcock 47, for example, attached at the end of the tube in order to inflate and deflate the collar 38. The syringe 46 can be employed to supply a suitable fluid, such as air, a saline solution or other substantially biocompatible gas or liquid material, for inflating the collar 38.

As illustrated in FIG. 4, once the inlet portion 16 has been inserted through the incision 30 in the blood vessel 34 and the inlet opening 18 has been properly positioned in the blood vessel, the collar 38 can be inflated by means of the flexible tube 44. The solution can be introduced into the chamber 42 through the flexible tube 44, thereby expanding the collar 38 radially outward against the wall 32 of the blood vessel 34 and forming a first sealing connection with the blood vessel at a first location 47. Blood in the downstream region 48 of the blood vessel 34 is thereby blocked from flowing around an exterior portion of the collar 38 to the upstream region 50 of the blood vessel, and instead is diverted into the inlet opening 18 and through the vascular shunt 10.

For the example of a carotid shunt, the vascular shunt 10 can define a passageway of circular cross-section having an interior diameter of approximately 0.25 inches. Those skilled in the art will understand and appreciate that other diameters can be used to provide vascular shunts according to an aspect of the present invention.

The outlet portion 20 is adapted for insertion into the incision 30, such as upstream of the portion 36 of the blood vessel 34 to be operated upon. Part of the outlet portion 20 has an enlarged cross-sectional area 52 (e.g., a bulge, a generally toroidal protrusion, etc.) for forming a second sealing connection at a second location 54 in the blood vessel 34. For example, the enlarged area 52 can be a soft flexible material, such as silicone or other polymer, which is fixed to the tube (e.g., by adhesion or friction) at a desired location spaced from the opening 22. The enlarged cross-sectional area 52 of soft flexible material is more compliant (e.g., it compresses more easily under force) than the tubular structure of the shunt 10. The enlarged area 52 can be a material that is softer than the body of the shunt, such as to mitigate damage to the vessel as it is urged into the vessel, as shown in FIGS. 2 and 3. The enlarged area can be either a solid or hollow member that encircles the outlet portion of the shunt 20.

In the example shown in FIGS. 1–3, the enlarged area 52 encircles at least a substantial part of the circumference of the outlet portion 20 near, but at a location spaced apart from the opening 22. The enlarged cross-sectional area 52 has a generally fixed cross-sectional dimension, which can be formed as part of the tube or be another structure attached about the second end portion near the opening 22. In the illustrated example, the enlarged cross-sectional area 52 has its largest cross-section near its middle and tapers curves from the middle to the ends of the area to a cross-section that generally approximates the cross-section of the tube at such ends.

By way of example, subsequent to the inlet portion 16 being positioned at the first location 47, the balloon being inflated to form the first sealing connection, and air being bled out of the vascular shunt 10, the outlet portion 20 is inserted into the blood vessel 34 at the second location 54. An outer surface 56 of the enlarged area 52 engages the wall 32 of the blood vessel 34 and creates the second sealing connection.

The outlet portion 20 can further have a plurality of visual indicators (or indicia) 57 for displaying to the surgeon the depth of insertion of the outlet portion (See FIG. 2). The indicators 57 are, for example, spaced at one centimeter increments upstream of the enlarged area 52, as measured from the distal end of the enlarged area.

In accordance with another aspect of the present invention, the outlet portion 20 can further include an opening 58 extending between an inner surface 60 of the outlet portion 20 and an outer surface 62 of the outlet portion. For example, the opening 58 can be a circumferentially extending, generally circular opening formed through the sidewall 40 located adjacent a distal end of the opening 58. When the outlet portion 20 is positioned at the second location 54 of a blood vessel 34 (e.g., the carotid artery), blood can flow downstream through the opening 58 and along the outer surface 62 of the outlet portion 20. This other stream of blood flow helps mitigate occlusion of the blood vessel 34 near the end portion 20 of the shunt 10.

The vascular shunt 10 is flexible and thus can easily be bent while positioning it at the surgical site. As viewed in FIGS. 2 and 3, the vascular shunt 10 can be completely inserted in the area of the blood vessel 34 to be operated upon (FIG. 2), or it may be looped in order to pickup any extra length of the vascular shunt (FIG. 3). For example, the vascular shunt 10 is formed of flexible plastic material, such a polyvinyl chloride or plastisol. However, alternative non-toxic flexible, fluid-tight materials can also be employed in accordance with an aspect of the present invention.

Blood flowing through the vascular shunt 10 is pulsatile, such as caused by pressure velocity variations resulting from blood flow due to the pumping of the heart. The pressure velocity variations due to the flow of blood, when amplified to an audible level, provides a distinct sound well known to surgeons and other medical professionals. This sound thus can provide an indication as to whether blood is flowing through the shunt adequately.

In accordance with another aspect of the present invention, a transducer 64 can be operatively associated with vascular shunt 10. For example, the transducer 64 can be attached to the exterior wall 66 adjacent to the branch portion 26 by suitable means, such as adhesive. The transducer 64 should be attached by means which will not only securely fasten the transducer to the vascular shunt 10, but also facilitate transmission of ultrasonic waves from within the shunt to the transducer (e.g., introduce minimum sound attenuation). Alternatively, the transducer 64 can be formed integrally within at least a portion of the sidewall of the shunt 10. The transducer 64 can be located adjacent the intersection of the branch portion 26 and the intermediate portion 24 fixed to the intermediate portion of the tube.

By way of example, the transducer 64 is a piezo-electric crystal pick-up sensitive to pressure velocity variations caused by the flow of blood through the shunt 10 in response to the beating heart of the patient. The electric signals produced by the transducer 64 can be transmitted to an associated electronic circuit 67 (FIG. 2) remote from the transducer by a direct wire connection. The wire 68 extends away from the transducer 64 along the branch portion 26 and can terminate with a plug-type connector 70 (e.g., a male or female connector part). The connector 70 allows easy electrical hook-up once the vascular shunt 10 is positioned at the surgical site.

By way of further example, the transducer 64 generates electrical signals corresponding to pressure variations within the shunt that operate on the transducer. The wire 68 and connector 70 can communicate the electrical signals to a conventional amplifier 72, which is operative to amplify the signals to a desired level to facilitate their conversion into audible sound. For example, the amplified electric signals are then communicated to an audio device 74, such as a speaker, for audibly informing the surgeon of the status of the blood flow in the shunt.

It is to be understood and appreciated that because the transducer 64 of the shunt provides simple electrical signals that can be directly converted to audio-only status information, no other electronic equipment is necessary to obtain such information and convert it to audio. As a result, the cost of the shunt and associated monitoring equipment can be significantly less than traditional complicated monitoring equipment, which employs multiple transducers to obtain information and processors to compute the flow rate. The audible indication of flow status through a shunt according to an aspect of the present invention further means that the surgeon need not look away from the surgical site to receive any data in this manner. It is to be further appreciated that the combination of piezo-electric crystal with vascular catheters for monitoring should have a widespread application in cardiovascular medicine.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A vascular shunt apparatus comprising:

an elongate tubular member having first and second end portions spaced apart by a length of an intermediate portion, an aperture extending axially through the tubular member between the first and second portions;

the first end portion being adapted to form a first sealing connection with a fluid carrying system at a first location, the second end portion being adapted to form a second sealing connection with the fluid carrying system at a second location spaced apart from the first location to facilitate fluid flow through the aperture of the tubular member between the first and second locations;

a single piezo-electric crystal connected with the tubular member for monitoring the fluid flow through the tubular member, the single piezo-electric crystal being configured provide an electrical signal in response to flow of fluid through the tubular member; and an electrical circuit electrically connected with the single piezoelectric crystal, the electrical circuit being configured to convert the electrical signal provided by the single piezo-electric crystal to an audible sound corresponding to the flow of fluid through the tubular member.

2. The apparatus of claim 1, further comprising a length of an electrical wire electrically coupled with the single piezo-electric crystal, the wire extending from the single piezoelectric crystal and terminating in a connector configured to couple to electrical circuit, the electrical signal provided by the single piezo-electric crystal being communicated through the wire to the connector.

3. The apparatus of claim 2, wherein the electrical circuit further comprises:

an amplifier coupled to the connector to receive the electrical signal from the single piezo-electric crystal, the amplifier amplifying the electrical signal to provide an amplified electrical signal; and an audio device that converts the amplified electrical signal to the audible sound corresponding to the flow of fluid through the tubular member.

4. The apparatus of claim 3, wherein the connector is a first connector part, the apparatus further comprising a second connector part configured to electrically connect the first connector part with the amplifier.

5. The apparatus of claim 1, the first end portion further comprising an genetally fixed, enlarged portion having an enlarged cross-section relative to portions of the tubular member on axially opposed sides of the enlarged portion, the enlarged portion being dimensioned and configured to form the first sealing connection.

6. The apparatus of claim 5, the enlarged portion comprising a generally soft, flexible material that is more compliant than the elongate tubular member.

7. The apparatus of claim 5, the second end portion further comprising an inflatable collar that can, upon being inflated, form the second sealing connection.

8. The apparatus of claim 5, further comprising an opening extending through a sidewall of the first end portion of the tubular member between the enlarged portion and an open end of the first end portion to mitigate occlusion within the fluid carrying system.

9. The apparatus of claim 1, further comprising a tubular branch portion extending away from the intermediate portion of the tubular member, the tubular branch portion having an aperture that is in fluid communication with the aperture of the tubular member.

10. The apparatus of claim 9, wherein the single piezo-electrical crystal is fixed to the intermediate portion of the tubular member at a location that is adjacent to an intersection of the tubular branch portion and the intermediate portion of the tubular member.

11. A vascular shunt apparatus comprising:
an elongate tubular member having spaced apart inflow and outflow ends, an aperture extending axially through the tubular member between the first and second ends;
a portion of the tubular member located proximal the outflow end having an enlarged cross-section relative to portions of the tubular member on axially opposite sides adjacent to the enlarged cross-sectional portion;
a single piezo-electric crystal operatively connected with the tubular member and configured to provide an electrical signal in response to fluid flow through the tubular member;
an amplifier configured to receive the electrical signal and to amplify the electrical signal to a desired level; and
a speaker configured to directly convert the amplified electrical signal to an audible sound indicating the flow of fluid through the tubular member.

12. The apparatus of claim 11, further comprising a length of a wire that provides the electrical signal from the single piezo-electric crystal to the amplifier.

13. The apparatus of claim 12, wherein the wire extends from the single piezo-electric crystal and terminates in one of a male or female connector part, the apparatus further comprising another one of the male or female connector part, the male and female connector parts being configured to electrically connect the wire with the amplifier.

14. The apparatus of claim 11, further comprising an inflatable collar located near the inflow end of the tubular member to provide a substantially sealing connection with a blood vessel.

15. The apparatus of claim 14, further comprising a flexible tube in fluid communication with the inflatable collar to facilitate inflating the inflatable collar.

16. The apparatus of claim 11, further comprising a branch portion for selectively bleeding air out of the tubular member, the branch portion extending away from the intermediate portion.

17. The apparatus of claim 16, wherein the single piezo-electrical crystal is fixed to the intermediate portion of the tubular member at a location that is adjacent to an intersection of the tubular branch portion and the intermediate portion of the tubular member.

18. The apparatus of claim 11, the outflow end tapering along an axial length thereof to define a tapered outlet configured to facilitate insertion thereof into a blood vessel.

19. The apparatus of claim 11, wherein at least a length of the tubular member near the outflow end further comprises a plurality of indicators for displaying a depth of insertion of the tubular member into a blood vessel.

20. A vascular shunt apparatus comprising:
an elongate tubular member having first and second end portions spaced apart by a length of an intermediate portion, an aperture extending axially through the tubular member between the first and second end portions;
the first end portion being adapted to form a first sealing connection with a fluid carrying vascular system at a first location;
the second end portion being adapted to form a second sealing connection with the fluid carrying vascular system at a second location spaced apart from the first location to facilitate fluid flow through the aperture of the tubular member between the first and second locations;
a single piezo-electric crystal operatively associated with the tubular portion for monitoring the fluid flow through the aperture of the tubular member, the single piezo-electric crystal configured to provide an electrical signal in response to flow of fluid through the tubular member, the electrical signal being indicative the flow of fluid through the tubular member;
an electronic circuit remote from the single piezo-electric crystal, the electronic circuit being configured to amplify and convert the electrical signal to an audible sound indicative of flow through the tubular member; and
a wire connection for communicating the electrical signal from the single piezo-electric crystal to the electrical circuit.

* * * * *

UNITED STATES PATENT AND TRADEMARK OFFICE
CERTIFICATE OF CORRECTION

| | | |
|---|---|---|
| PATENT NO. | : 7,087,034 B2 | Page 1 of 1 |
| APPLICATION NO. | : 10/247601 | |
| DATED | : August 8, 2006 | |
| INVENTOR(S) | : William E. McPherson and Walter Smithwick | |

It is certified that error appears in the above-identified patent and that said Letters Patent is hereby corrected as shown below:

In Claim 5, Column 6, Line 47, change "an genetally" to -- "a generally" --.

Signed and Sealed this

Twenty-third Day of January, 2007

JON W. DUDAS
*Director of the United States Patent and Trademark Office*